(12) United States Patent
Arnin et al.

(10) Patent No.: US 10,736,753 B2
(45) Date of Patent: Aug. 11, 2020

(54) IMPLANT DELIVERY SYSTEM

(71) Applicant: Zygofix Ltd., Misgav (IL)

(72) Inventors: Uri Arnin, Kiryat Tivon (IL); Ofer Levy, Binyamina (IL)

(73) Assignee: ZYGOFIX LTD., Misgav (IL)

( * ) Notice: Subject to any disclaimer, the term of this patent is extended or adjusted under 35 U.S.C. 154(b) by 154 days.

(21) Appl. No.: 15/832,928

(22) Filed: Dec. 6, 2017

(65) Prior Publication Data

US 2019/0167445 A1   Jun. 6, 2019

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61F 2/44* | (2006.01) |
| *A61F 2/30* | (2006.01) |
| *A61B 17/92* | (2006.01) |
| *A61B 17/17* | (2006.01) |

(52) U.S. Cl.
CPC ............ *A61F 2/4603* (2013.01); *A61F 2/447* (2013.01); *A61F 2/4611* (2013.01); *A61B 17/1757* (2013.01); *A61B 17/92* (2013.01); *A61B 2017/927* (2013.01); *A61F 2/442* (2013.01); *A61F 2/4405* (2013.01); *A61F 2/4455* (2013.01); *A61F 2002/3011* (2013.01); *A61F 2002/30108* (2013.01); *A61F 2002/30121* (2013.01); *A61F 2002/30123* (2013.01); *A61F 2002/30166* (2013.01); *A61F 2002/30179* (2013.01); *A61F 2002/30303* (2013.01); *A61F 2002/4625* (2013.01); *A61F 2002/4627* (2013.01); *A61F 2002/4681* (2013.01); *A61F 2002/4687* (2013.01)

(58) Field of Classification Search
None
See application file for complete search history.

(56) References Cited

U.S. PATENT DOCUMENTS

| | | | |
|---|---|---|---|
| 2004/0243240 A1* | 12/2004 | Beaurain | A61F 2/4425 623/17.14 |
| 2006/0036261 A1 | 2/2006 | McDonnell | |
| 2007/0118224 A1 | 5/2007 | Shah | |
| 2009/0312763 A1* | 12/2009 | McCormack | A61B 17/025 606/83 |
| 2014/0200668 A1 | 7/2014 | Kirschman | |

FOREIGN PATENT DOCUMENTS

| | | |
|---|---|---|
| EP | 1124510 | 8/2001 |
| EP | 1563808 | 8/2005 |
| EP | 3195832 | 7/2017 |
| FR | 2887762 | 1/2007 |

OTHER PUBLICATIONS

PCT Search Report PCT/IB2018/059668, dated Apr. 11, 2019.

* cited by examiner

*Primary Examiner* — Sameh R Boles
(74) *Attorney, Agent, or Firm* — Dekel Patent Ltd.; David Klein

(57) ABSTRACT

A delivery device includes a guide tool and an impact tool. The guide tool includes an elongate body formed with a longitudinal guide channel, whose inner perimeter is made to complement an outer contour of an implant. The elongate body is formed with a longitudinal impact-tool channel, whose inner perimeter is made to complement an outer contour of the impact tool.

8 Claims, 3 Drawing Sheets

IMPLANT DELIVERY SYSTEM

FIELD OF THE INVENTION

The present invention relates generally to spinal implants and prostheses, and particularly to a delivery system for deployment of a spinal implant which has flexibility, pivoting or folding characteristics.

BACKGROUND OF THE INVENTION

There are many anatomical geometrical changes between one individual and another. A joint shape can vary between individuals and even between the joints in the same individual. Devices that are designed to be inserted into a certain joint space should therefore include means to adapt the geometry to suit the particular joint. For example, a device may have a straight shape, and as it is forced into the joint space, it must bend according to the arcuate joint space.

However, the insertion of the device into the joint space may require application of impact in order for the device to enter the joint space. The application of the impact may cause the device to bend before it properly enters the joint space. This may cause the procedure to fail, either because the bending of the device prevents its entry or the device may break as it bunches or buckles upon entry into the body lumen.

SUMMARY OF THE INVENTION

The present invention seeks to provide a device and method for the guidance and protection of an implant that is bendable, flexible or pivotable during its delivery into a confined body cavity or lumen.

In one non-limiting embodiment, the delivery device includes a guide tool to channel and guide the implant out from the distal end of the tool into the lumen opening. The guide tool may include a sleeve with an internal geometry, which is precisely designed to house the implant with minimal gaps between them. The sleeve geometry allows the implant to move from the proximal to the distal end of the guide tool. The tight tolerances around the implant eliminate the risk of breakage or kinking throughout the motion. As the implant starts to exit from the sleeve and enter the lumen, it is released from the sleeve's constraints and is capable of adjusting to the anatomy as intended.

The delivery device may also include an impact tool for application of an external impact on the implant to help the implant enter the body lumen.

Without limitation, the delivery device has the following characteristics:
1. Ability to guide the implant into the body lumen.
2. Ability to channel and guide the implant from a point accessible to the user into the lumen opening.
3. Ability to protect the implant from kinking and breakage throughout the guidance until confined in the body cavity.
4. Ability to maintain distraction of the body cavity and resist its collapse in order to assist in the insertion process.
5. Ability to apply impact on the implant to force its insertion into the cavity.

There is thus provided in accordance with an embodiment of the invention a delivery device including a guide tool and an impact tool, the guide tool including an elongate body formed with a longitudinal guide channel, whose inner perimeter is made to complement an outer contour of an implant, the elongate body being formed with a longitudinal impact-tool channel, whose inner perimeter is made to complement an outer contour of the impact tool.

In accordance with an embodiment of the invention the guide channel and the impact-tool channel overlap each other at a central portion of the elongate body.

In accordance with an embodiment of the invention a distal end of the guide tool is formed with distraction members, which protrude distally from the distal end of the guide tool.

In accordance with an embodiment of the invention a guide tongue protrudes distally from a distal end of the guide tool.

In accordance with an embodiment of the invention the impact tool includes a proximal handle extending from a proximal end of a shaft, the handle being capable of receiving hammer blows to drive an implant into a body lumen.

BRIEF DESCRIPTION OF THE DRAWINGS

The present invention will be understood and appreciated more fully from the following detailed description, taken in conjunction with the drawings in which.

DETAILED DESCRIPTION

Figure 1:
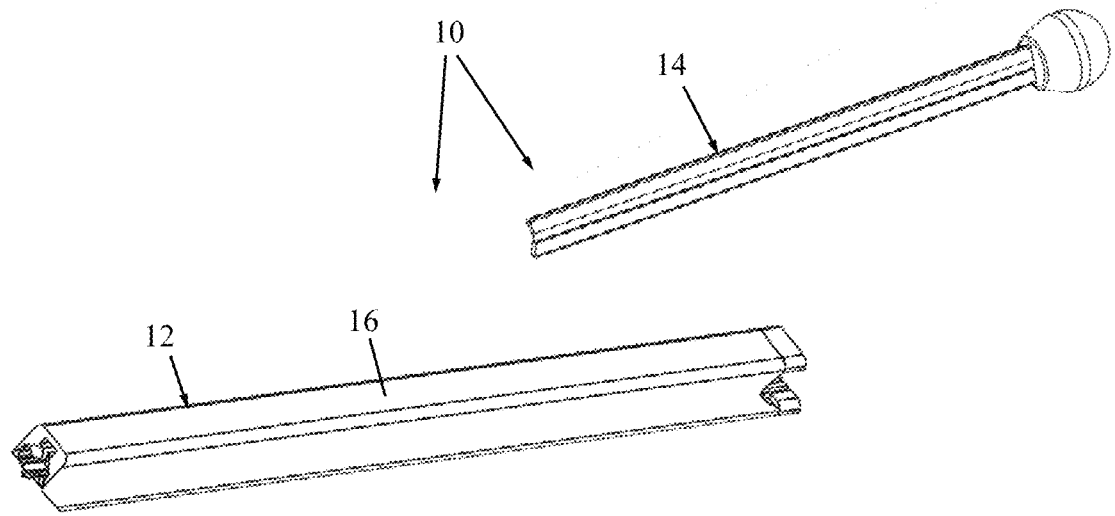
FIG. 1 is a simplified pictorial illustration of a delivery device, constructed and operative in accordance with a non-limiting embodiment of the present invention, including a guide tool and an impact tool.

Reference is now made to FIG. 1, which illustrates a delivery device 10, constructed and operative in accordance with a non-limiting embodiment of the present invention. Delivery device 10 includes a guide tool 12 and an impact tool 14.

Figure 2:
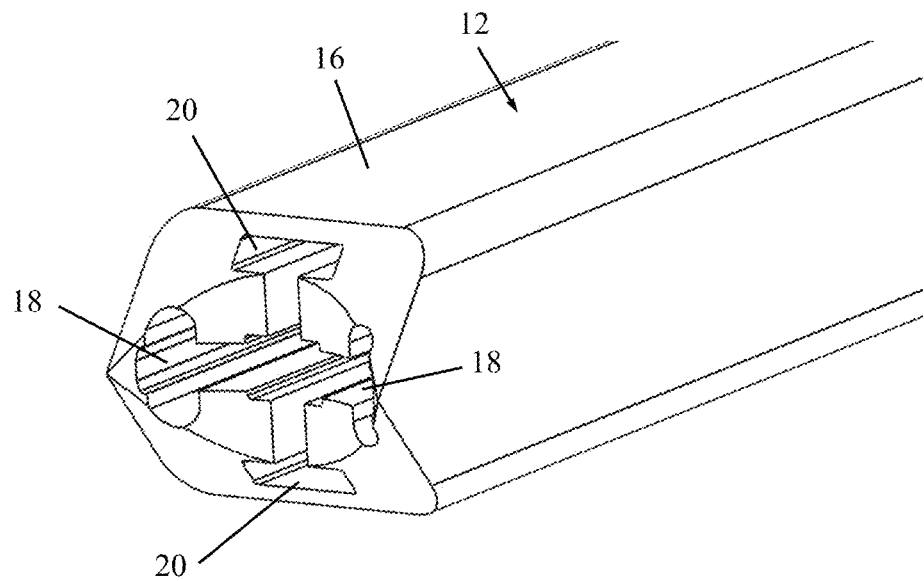
FIG. 2 is a simplified pictorial illustration of the proximal end of the guide tool, showing an entry port for inserting the implant to be delivered.

As seen better in FIG. 2, guide tool 12 includes an elongate body (sleeve) 16 formed with a longitudinal guide channel 18, whose inner perimeter is made to complement the outer contour of an implant. The elongate body 16 is also formed with a longitudinal impact-tool channel 20, whose inner perimeter is made to complement the outer contour of impact tool 14. The guide channel 18 and the impact-tool channel 20 may overlap each other at a central portion of the elongate body 16.

Figure 3:
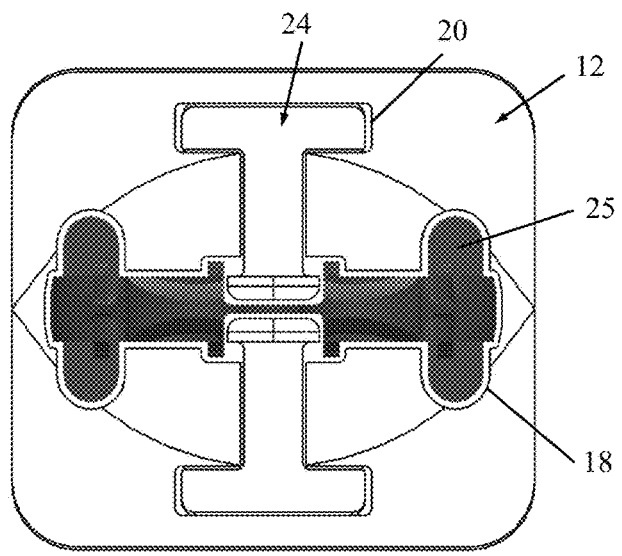
FIG. 3 is a simplified end-view illustration of the proximal end of the guide tool with an implant inserted therein.

FIG. 3 illustrates an implant 25 inserted in guide channel 18 and impact tool 14 inserted in impact-tool channel 20.

Figures 4A, 4B:
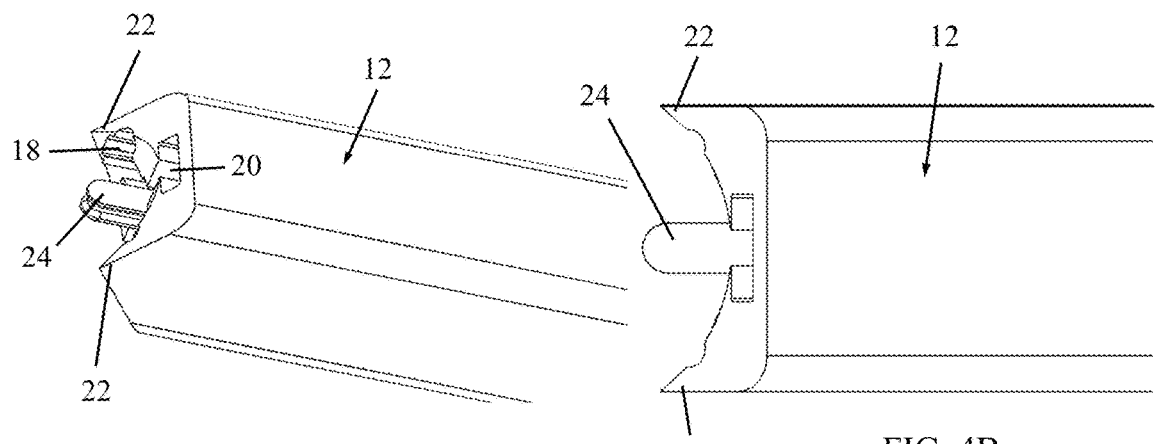
FIGS. 4A and 4B are simplified pictorial and side-view illustrations, respectively, of the distal end of the guide tool.
Figure 5:
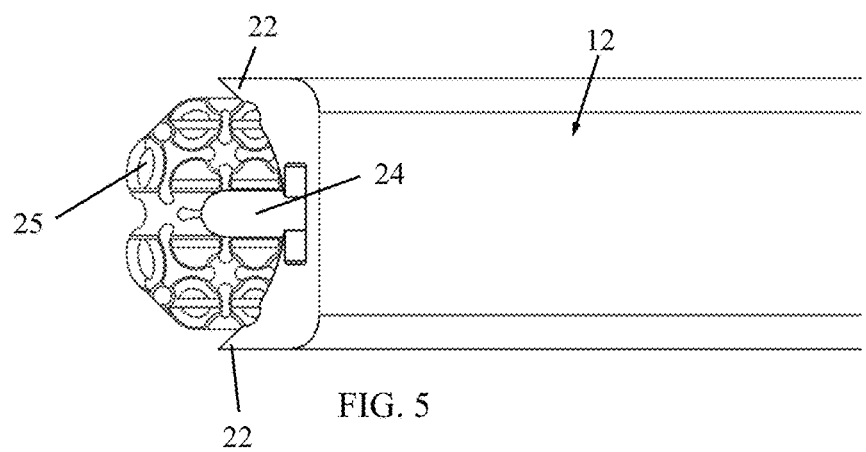
FIG. 5 is a simplified pictorial illustration of the implant exiting the distal end of the guide tool.

Reference is now made to FIGS. 4A and 4B, which illustrate a distal end of guide tool 12. The distal end may be formed with distraction members 22, which may be sharp or blunt lips that protrude distally from the distal end of guide tool 12. Optionally, a guide tongue 24 may protrude distally from the distal end of guide tool 12. The guide tongue 24 may help support and guide the implant upon emergence from the distal end of guide tool 12 (as seen in FIG. 5) and/or support and guide the impact tool 14 when it passes through the distal end of guide tool 12.

Figure 6:
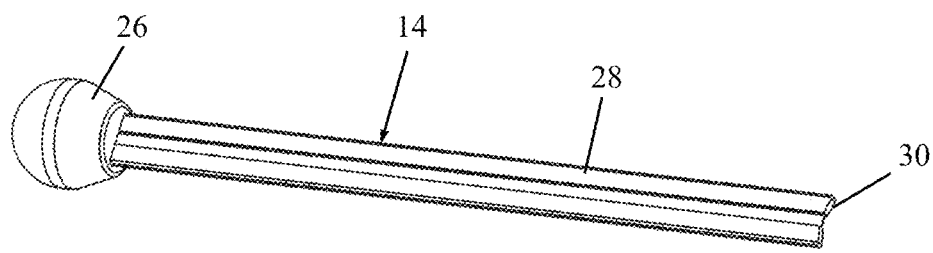
FIG. 6 is a simplified pictorial illustration of the impact tool of the delivery device.

Reference is now made to FIG. 6, which illustrates impact tool 14. Impact tool 14 has a proximal handle 26, a shaft 28 and a distal end 30. Handle 26, which extends from the proximal end of shaft 28, is capable of receiving hammer blows to drive the implant into a body lumen.

Figure 7:
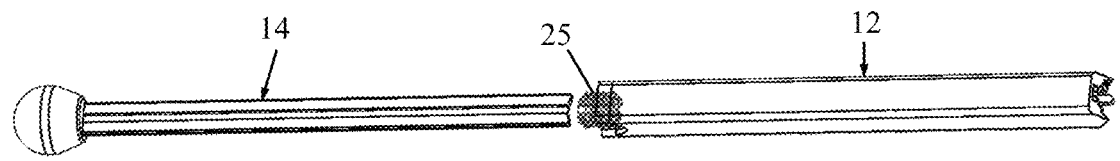
FIG. 7 is a simplified pictorial illustration of a delivery device, showing the impact tool about to strike the implant inserted in the proximal end of the guide tool.

Reference is now made to FIG. 7, which illustrates the delivery device, wherein impact tool 14 is poised to strike (impact against) the implant 25 inserted in the proximal end of guide tool 12.

The motion of implant 25 through the sleeve is guided by the guide channel, which is designed to have a minor tolerance between its inner perimeter and the outer contour of implant 25, thereby preventing any kinking or breakage of implant 25.

The invention claimed is:

1. A delivery device comprising:
a guide tool and an impact tool, said guide tool comprising an elongate body formed with a longitudinal guide channel, whose inner perimeter is made to complement an outer contour of an implant, said elongate body being formed with a longitudinal impact-tool channel, whose inner perimeter is made to complement an outer contour of said impact tool, wherein said guide channel and said impact-tool channel overlap each other at a central portion of said elongate body, wherein said guide channel comprises first portions on opposite sides of a central longitudinal axis of said elongate body and second portions that extend perpendicularly from ends of said first portions distanced from said central longitudinal axis.

2. The delivery device according to claim 1, wherein said guide channel and said impact-tool channel are overlapping and perpendicular to each other at said central portion of said elongate body.

3. The delivery device according to claim 1, wherein a distal end of said guide tool is formed with distraction members, which protrude distally from the distal end of said guide tool.

4. The delivery device according to claim 1, wherein a guide tongue protrudes distally from a distal end of said guide tool.

5. The delivery device according to claim 1, wherein said impact tool comprises a proximal handle extending from a proximal end of a shaft, said handle being capable of receiving hammer blows to drive an implant into a body lumen.

6. The delivery device according to claim 1, wherein said guide channel comprises non-symmetrical portions on opposite sides of a central longitudinal axis of said elongate body.

7. The delivery device according to claim 1, wherein said impact-tool channel comprises first portions on opposite sides of a central longitudinal axis of said elongate body and second portions that extend perpendicularly from ends of said first portions distanced from said central longitudinal and said second portions of said guide channel are shaped differently than said second portions of said impact-tool channel.

8. A delivery device comprising:
a guide tool and an impact tool, said guide tool comprising an elongate body formed with a longitudinal guide channel, whose inner perimeter is made to complement an outer contour of an implant, said elongate body being formed with a longitudinal impact-tool channel, whose inner perimeter is made to complement an outer contour of said impact tool, wherein said guide channel and said impact-tool channel overlap each other at a central portion of said elongate body, wherein said impact-tool channel comprises first portions on opposite sides of a central longitudinal axis of said elongate body and second portions that extend perpendicularly from ends of said first portions distanced from said central longitudinal axis.

* * * * *